(12) United States Patent
Limaye et al.

(10) Patent No.: US 11,471,612 B2
(45) Date of Patent: Oct. 18, 2022

(54) INDUCTION HEATING CIRCUIT FOR MEDICAL SHARPS REMOVAL DEVICE

(71) Applicant: Becton, Dickinson and Company, Franklin Lakes, NJ (US)

(72) Inventors: Amit Limaye, Wayne, NJ (US); David Schiff, Highland Park, NJ (US); Todd Zielinski, Philadelphia, PA (US); Nick McGill, Broomall, PA (US); Marian Morys, Downingtown, PA (US); Glenn Smollinger, Eagleville, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 381 days.

(21) Appl. No.: 16/628,953

(22) PCT Filed: Jun. 22, 2018

(86) PCT No.: PCT/US2018/039039
§ 371 (c)(1),
(2) Date: Jan. 6, 2020

(87) PCT Pub. No.: WO2019/010019
PCT Pub. Date: Jan. 10, 2019

(65) Prior Publication Data
US 2020/0222639 A1     Jul. 16, 2020

Related U.S. Application Data

(60) Provisional application No. 62/529,926, filed on Jul. 7, 2017, provisional application No. 62/530,001, filed on Jul. 7, 2017.

(51) Int. Cl.
*H05B 6/10* (2006.01)
*A61M 5/32* (2006.01)
(Continued)

(52) U.S. Cl.
CPC ......... *A61M 5/3205* (2013.01); *B09B 3/0075* (2013.01); *H05B 6/06* (2013.01);
(Continued)

(58) Field of Classification Search
CPC .......... H05B 1/025; H05B 6/06; H05B 6/101; H05B 6/36; H05B 6/80; A61M 5/3205;
(Continued)

(56) References Cited

U.S. PATENT DOCUMENTS

| 3,753,412 A | 8/1973 | Shepard et al. |
| 4,268,364 A | 5/1981 | Moriconi et al. |

(Continued)

FOREIGN PATENT DOCUMENTS

CN        104185327 B      2/2016

OTHER PUBLICATIONS

Partial Supplementary European Search Report dated Jan. 25, 2021, which issued in the corresponding European Patent Application No. 18827968.1.

*Primary Examiner* — Hung D Nguyen
(74) *Attorney, Agent, or Firm* — Dickinson Wright PLLC

(57) ABSTRACT

Induction heating from an induction coil (108) is used to separate a metal medical sharp (144) from its holder (142) by applying a high-frequency oscillating magnetic field that excites eddy currents and resistance heating in the sharp. The heated metal sharp melts the adhesive or plastic securing the sharp to its holder. The use of induction heating is advantageous in that it does not require direct contact between the electrical circuit and the sharp or its holder. The heating can also act to sterilize the sharp and thereby render it less hazardous at the same time that it separates the sharp from its holder. The induction coil can have a stepped or conical shape to concentrate the RF energy at the interface between the metal sharp and its holder.

24 Claims, 12 Drawing Sheets

(51) Int. Cl.
  *B09B 3/00* (2022.01)
  *H05B 6/06* (2006.01)
  *H05B 6/36* (2006.01)

(52) U.S. Cl.
  CPC ............... *H05B 6/101* (2013.01); *H05B 6/36* (2013.01); *A61M 2005/3206* (2013.01); *A61M 2005/3209* (2013.01); *A61M 2205/50* (2013.01); *A61M 2205/8206* (2013.01); *A61M 2205/8243* (2013.01)

(58) Field of Classification Search
  CPC .............. A61M 5/3276; A61M 5/3278; A61M 5/3286; A61M 2205/332; A61M 2205/368; A61M 2205/50; A61M 2205/8206; A61M 2205/8243; A61B 50/36; A61B 50/362; A61B 2017/00734; H01F 5/00; H01F 2005/006; B09B 3/0075; A61L 2/04; A61L 2202/24
  USPC ........ 219/68, 69.1, 201, 243, 364, 365, 366, 219/385, 645, 674
  See application file for complete search history.

(56) References Cited

U.S. PATENT DOCUMENTS

| | | | |
|---|---|---|---|
| 4,867,309 A | 9/1989 | Germain | |
| 5,075,529 A | 12/1991 | Kudo | |
| 5,076,178 A * | 12/1991 | Kohl | A61M 5/3278 219/68 |
| 5,212,362 A * | 5/1993 | Burden | A61M 5/3278 219/68 |
| 5,277,868 A | 1/1994 | Langford | |
| 5,441,622 A | 8/1995 | Langford | |
| 5,545,869 A | 8/1996 | Piva | |
| 5,727,455 A | 3/1998 | Yerman | |
| 5,761,975 A | 6/1998 | Waluda | |
| 5,765,490 A * | 6/1998 | Colin | A61L 2/04 219/635 |
| 5,852,267 A | 12/1998 | Yanobu | |
| 5,968,402 A | 10/1999 | Lee | |
| 6,545,242 B1 | 4/2003 | Butler | |
| 7,001,472 B2 | 2/2006 | Collier et al. | |
| 7,513,363 B2 | 4/2009 | Brown et al. | |
| 7,971,715 B1 | 7/2011 | Fernandes et al. | |
| 8,829,394 B2 | 9/2014 | Limaye | |
| 9,579,469 B2 | 2/2017 | Limaye | |
| 9,802,006 B2 | 10/2017 | Limaye | |
| 2005/0121343 A1 | 6/2005 | Miller et al. | |
| 2006/0118553 A1 | 6/2006 | Terada et al. | |
| 2007/0215578 A1* | 9/2007 | Ito | A61M 5/3278 219/68 |
| 2009/0178943 A1 | 7/2009 | Oostman, Jr. et al. | |
| 2012/0311839 A1 | 12/2012 | Limaye | |
| 2016/0175542 A1 | 6/2016 | Kirby et al. | |

\* cited by examiner

INDUCTION HEATING CIRCUIT FOR MEDICAL SHARPS REMOVAL DEVICE

This application claims priority to U.S. Provisional Patent Application Ser. No. 62/529,926, filed on Jul. 7, 2017 and entitled "Medical Sharp Removal and Storage Device", and to U.S. Provisional Patent Application Ser. No. 62/530,001, filed on Jul. 7, 2017 and entitled "Induction Heating Circuit for Medical Sharps Removal Device", the entire disclosures of both of said applications being expressly incorporated herein by reference.

FIELD OF THE INVENTION

The present invention relates generally to an electrical control circuit for use with a device for removing a medical sharp from a holder using inductive heating. In particular, but not by way of limitation, the present invention relates to an electrical control circuit for use with a device for removing a metal pen needle cannula from a plastic pen needle hub by using inductive heating to heat the metal cannula and melt the adhesive or plastic securing the cannula to the hub, and to an inductive heating coil for use in such a circuit. The control circuit and device can also be used to remove a metal syringe needle from a plastic needle hub or plastic syringe barrel, a metal lancet from a plastic lancet holder, or a metal introducer needle from a plastic needle hub in a catheter assembly.

BACKGROUND OF THE INVENTION

After a medical sharp, such as an injection pen needle, syringe needle, hypodermic needle, lancet or catheter introducer needle, has been used, it is desirable to remove and store the sharp in a safe container for several reasons. For example, the medical sharp often dulls after a single use, so subsequent use may cause discomfort to the patient. Additionally, multiple use of the medical sharp can also reduce the strength of the sharp, which may cause a potential fracture. Further, medical sharp reuse increases sanitary concerns and health risks to the patient. Moreover, exposed medical sharps can pose a health risk to patients, caregivers, and waste management workers.

A sharps container for storing used needles, which is known in the art, includes an inner box member and an outer housing member. The box and the housing each have an aperture that is dimensioned to receive a hypodermic needle. The box and the housing are hingedly connected to each other so that in an open position the apertures of the box and the housing overlap and the needle may be inserted through both of the apertures to project into the box. After the needle has been inserted into the apertures, the box and the housing are moved with respect to each other, for example in a scissor motion, so that the needle is clipped. After being clipped, the needle drops into the box for storage and subsequent disposal. Traditionally, the sharps container is a large red box, and insertion of the medical sharps is relatively easy, but removal of the medical sharps therefrom is purposefully difficult.

U.S. Pat. No. 6,545,242 to Butler discloses a device that, subsequent to insertion of a portion of a needle, heats at least a portion of the needle to approximately 1750° C., and then shears the needle, leaving a portion in the needle holder or hub. Similarly, U.S. Pat. No. 5,545,869 to Piva discloses a device that melts a portion of a blade or needle and cuts the stump of the blade or needle, leaving a portion of the blade or needle in the needle/blade holder or hub, Additionally, U.S. Pat. No. 4,867,309 to Germain discloses a device that holds a needle and its holder or hub by the needle stein, so that a user can twist the hub off of a syringe, or pull off the hub if the hub is friction-fitted on the syringe.

With each of these devices, however, a portion of the needle remains in the needle holder. Therefore, the potential for a needle-stick injury may remain. Additionally, the needle holder must be disposed of as medical waste, and cannot be recycled. Consequently, an improved medical needle removal device that removes the needle entirely is desirable. Storage of the removed needles is also desirable.

SUMMARY OF THE INVENTION

In accordance with an aspect of the present invention, induction heating is used to separate a metal medical sharp from its holder by applying a high-frequency oscillating magnetic field that excites eddy currents and resistance heating in the sharp. The use of induction heating is advantageous in that it does not require direct contact between the electrical circuit and the sharp or its holder, and the heating can also act to sterilize the sharp and thereby render it less hazardous at the same time that it separates the sham from its holder.

The separation of the sharp from its holder can be achieved in several ways, such as by melting all or part of the sharp, by locally heating the sharp so that it can be more easily cut or broken, by using the heated sharp to soften or melt an adhesive that attaches the sharp to its holder, or by using the heated sharp to soften or melt the adjoining plastic material of the holder itself. These methods can be used alone or in combination with each other, and can also be used in combination with mechanical separation methods.

One challenge in using induction heating to separate a metal medical sharp from its holder is that it is difficult to concentrate enough radio frequency (RF) energy in a small metallic body, such as a pen needle cannula, to produce the required softening or melting temperatures in a reasonably short period of time. Long energization times are undesirable not only because they are inconvenient to the user, but also because they can result in overheating of the induction coil.

Another challenge is that, while induction heating operates most efficiently at close range, some types of sharps holders, such as pen needle hubs, are physically large relative to the metal sharps themselves, and physically prevent the induction coil from being positioned close enough to the sharp for efficient energy transfer.

The oscillation frequency and/or amplitude can be increased to deliver more RF energy to the metal sharp in a given period of time, but the use of high frequencies and/or amplitudes can result in undesirable RF emissions and can also require regulatory approval in some cases.

In accordance with aspects of the present invention, these challenges are met in several ways. In one aspect, a specially shaped induction coil is used to maximize the efficiency of RF energy transfer to the metal sharp. The coil has a stepped shape, defined by two axially spaced portions having different diameters, and is useful for concentrating RF energy in metal pen needle cannulas that are mounted in hubs having similarly stepped shapes.

Another aspect of the present invention is the use of an oscillation frequency in the unlicensed industrial, scientific and medical (ISM) bands that allows for efficient energy transfer without introducing regulatory requirements or requiring the design of the needle removal device to block all undesirable RF emissions at these frequencies.

A still further aspect of the present invention lies in taking advantage of the RF "skin effect", which is the tendency of an alternating current (AC), in this case the eddy current induced by the induction coil, to become concentrated near the surface of the conductor in which the current is flowing. This effect becomes more pronounced at higher frequencies.

Since many types of medical sharps are designed in such a way that their outer surfaces are fitted or bonded into plastic holders, the skin effect is advantageous in efficiently directing RF energy to the specific part of the metal sharp (i.e., the metal/plastic interface) that requires heating in order to release the sharp from its holder.

BRIEF DESCRIPTION OF THE DRAWINGS

Additional aspects and advantages of embodiments of the present invention will be more readily appreciated from the following detailed description, taken in conjunction with the accompanying drawings, in which.

Throughout the drawings, like reference numerals are used to indicate like parts and components.

DETAILED DESCRIPTION OF EMBODIMENTS OF THE PRESENT INVENTION

Figure 1:
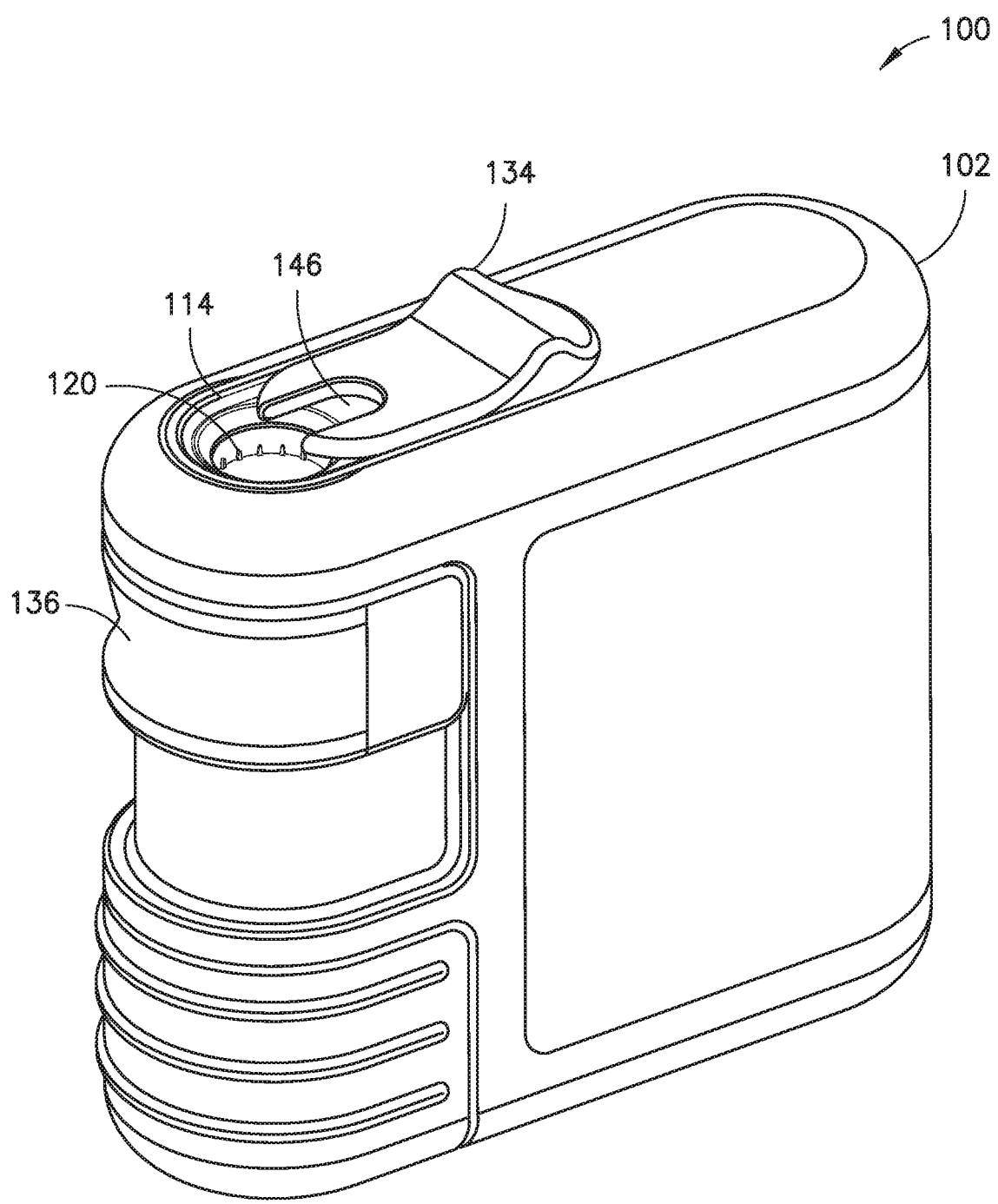
FIGS. 1 and 2 are perspective and cross-sectional views of a medical sharp removal and storage device in accordance with an embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or caned out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up", "down", "bottom", and "top" are relative, and are employed to aid illustration, but are not limiting.

Figure 2:
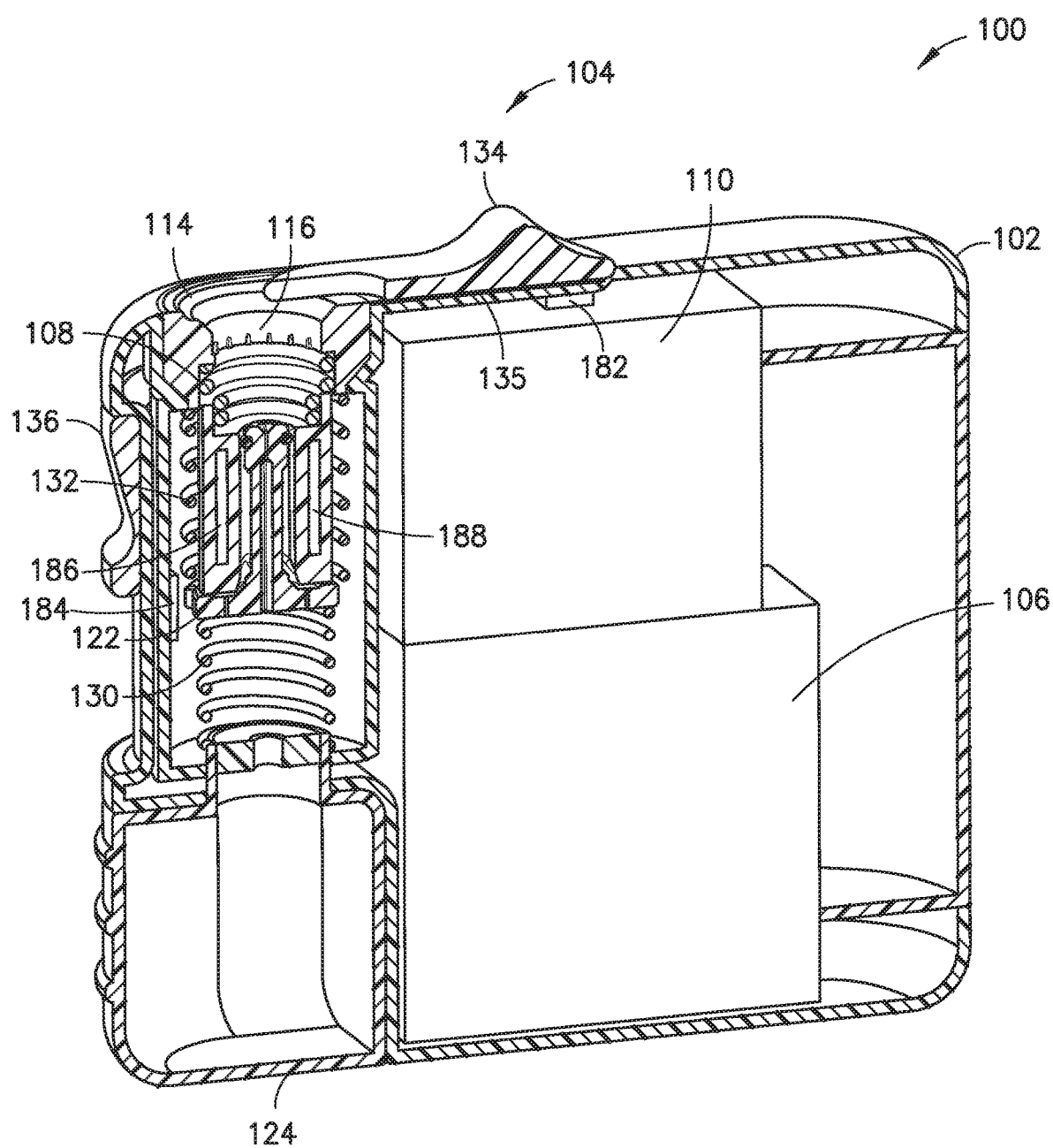

FIG. 1 is a perspective of an exemplary medical sharp removal and storage device 100 in accordance with an embodiment of the present invention, and FIG. 2 is a cross-sectional view of the device 100. The mechanical construction and operation of the device 100 is summarized below, and is described in more detail in U.S. Provisional Patent Application Ser. No. 62/529,926, filed on Jul. 7, 2017, which is incorporated herein by reference in its entirety.

The exemplary device 100 is adapted for use with single-use pen needles of the type typically used with reusable pen injectors, but can also be used with other types of medical sharps. As shown in the figures, the device 100 includes a body 102 and a heating unit 104. According to one embodiment, the heating unit 104 includes an energy source 106, such as a battery 106 or the like, an induction coil 108, and a controller 110, electrically connectable to the energy source 106 and the induction coil 108. The controller can include a printed circuit board, and can have circuit board components such as a memory chip and a microprocessor. The device 100 also includes a receiving unit 114 fixedly disposed in the body 102, a collet 122, a sharps receiving container or chamber 124, first and second biasing units 130 and 132, a door member 134, and a slider or user interface 136. In one embodiment, the sharps receiving container 124 is removable from the body 102.

Figure 3:
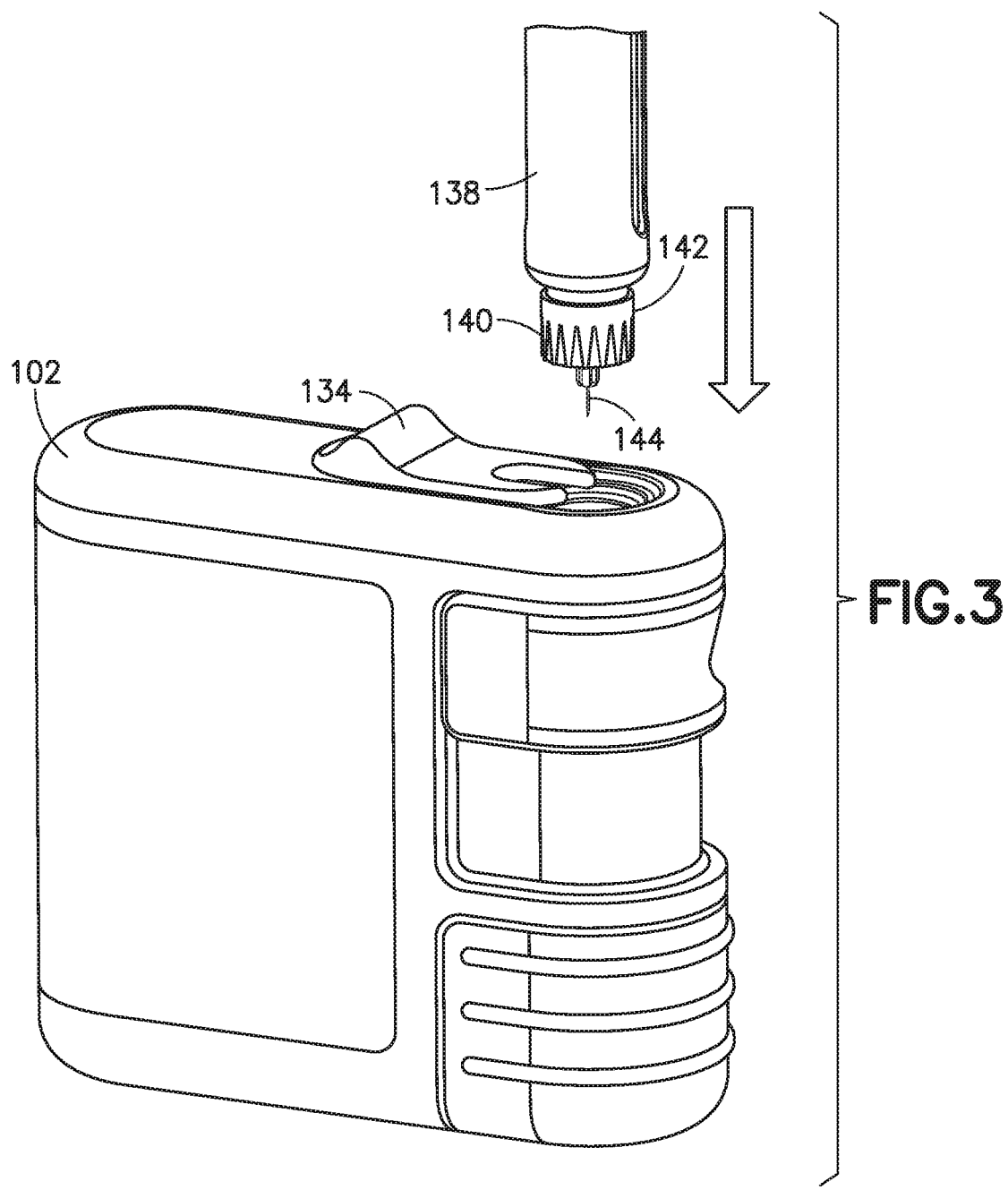
FIGS. 3 and 4 are perspective and cross-sectional views illustrating the operation of the exemplary device of FIGS. 1 and 2.
Figure 4:
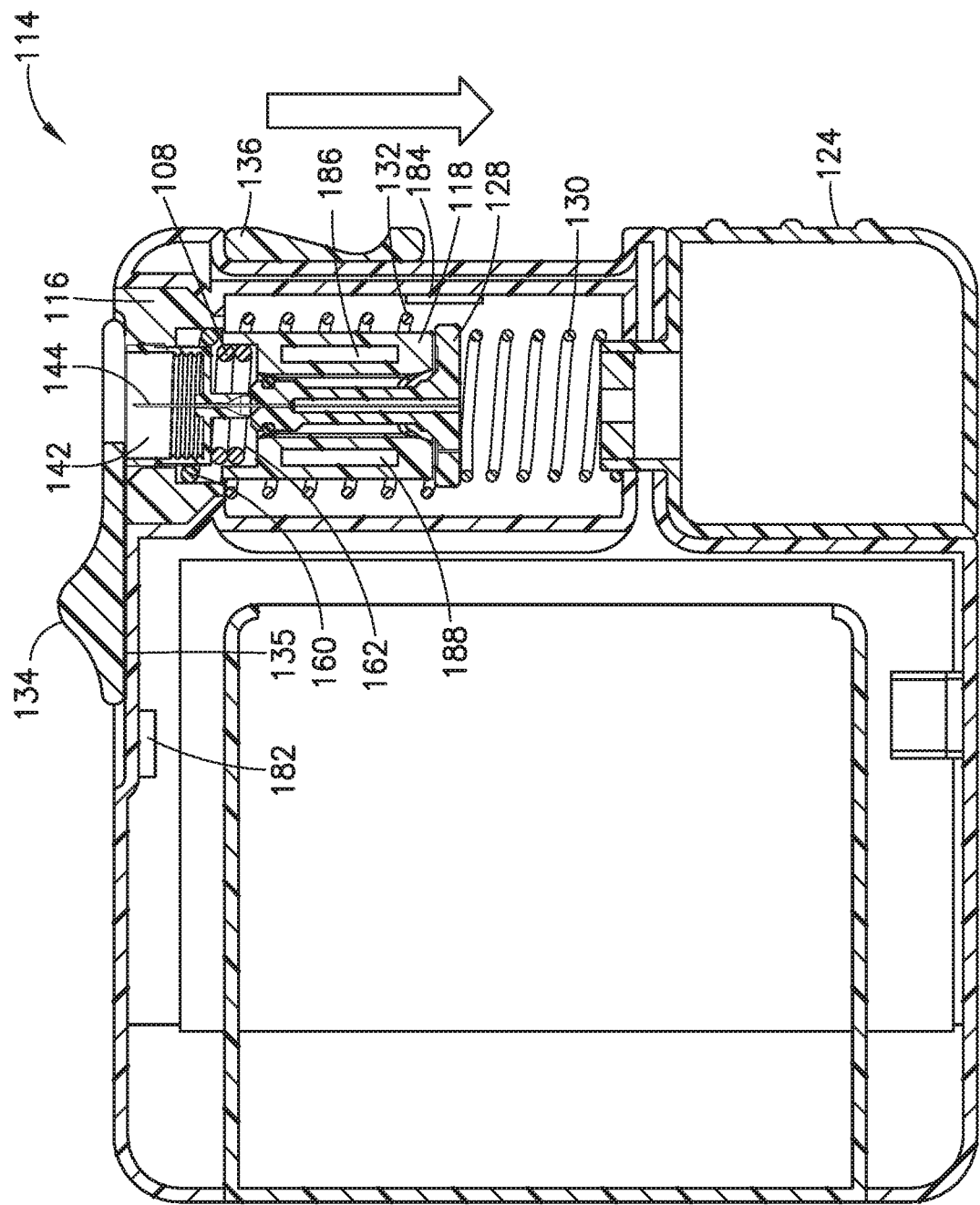

FIGS. 3 and 4 illustrate operation of the medical sharp removal and storage device 100. In FIG. 3, a user inserts a pen needle 140 connected to a pen injector 138 into the receiving portion 116 of the receiving unit 114. The pen needle 140 includes a plastic hub 142 and a medical sharp or needle cannula 144 made of metal, such as stainless steel. The splines of the pen needle engage the internal splines 120 of the receiving portion 116 to resist rotation of the pen needle 140, so that the user can unscrew the pen injector 138 from the pen needle 140 and remove the pen injector 138, leaving the pen needle 140 in the receiving portion 116 of the receiving unit 114.

When the user inserts the pen needle 140 into the receiving unit 114, the receiving portion 116 of the receiving unit 114 receives the hub 142, and the collet 122 receives the needle 144. As the user inserts the pen needle 140 into the receiving unit 114, the open collet 122 receives the needle 144. Subsequent to the user inserting the pen needle 140 into the receiving unit 114, the user closes the door member 134 by sliding the door member 134 forward relative to the body 102. The closed door member 134 aids in maintaining the pen needle 140 in the receiving unit 114, and the closed position of the door member 134 is sensed to enable the controller 110 to energize the induction coil 108. For example, there can be a physical or optical sensor 182 connected to the controller 110 that is triggered when the door member 134 reaches a closed position after a predetermined displacement relative to the body 102. Alternatively, the door member 134 can have an electrical contact that completes a portion of a circuit to between the controller 110 and the induction coil 108. Other methods of enabling the controller 110 to energize the induction coil 108 can be employed without departing from the scope of the present invention. In addition to these features, the lower surface of the door member 134 is provided with a conductive lining 135, preferably in the form of a metal foil or strip, that is connected to the ground or reference potential of the controller. This provides a shielding function that reduces undesirable RF emissions from the induction coil when the device is in operation.

Subsequent to the user closing the door member 134, the user slides the slider or user interface 136 down in a first direction, as shown by the arrow in FIG. 4. Although the user interface 136 is depicted as the slider 136, one skilled in the art will appreciate that other user interfaces, such as a release button, can be employed without departing from the scope of the present invention.

As shown in FIGS. 2 and 4, the second biasing unit or spring 132 is disposed on top of the lower flange of the collet 122 and the first biasing unit or spring 130 is disposed beneath the flange. Prior to displacement of the collet 122, the first spring 130 biases the collet 122 toward the receiving unit 114. In the initial state shown in FIG. 4, the second spring 132 also biases the collet 122 away the receiving unit 114. In this initial state, neither the first spring 130 nor the second spring 132 biases the collet 122. One skilled in the art will understand that by appropriately sizing the first and second biasing units 130 and 132, a desired force profile can be achieved for the force applied by a user on the slider 136 to operate the device 100.

The user interface or slider 136 is coupled to the collet 122. In one embodiment, the user interface or slider 136 is directly coupled to the collet 122. In another embodiment, another element, such as the second biasing unit or spring 132, is disposed between the user interface or slider 136 and the collet 122, and converts displacement of the slider 136 into displacement of the collet 122.

Displacement of the slider 136 by a predetermined distance causes the collet 122 to grip the needle 144 and also actuates the heating unit. According to one embodiment, the device 100 includes a mechanical or optical sensor 184 coupled to the controller 110 to determine when the predetermined displacement of the slider or user interface 136 has occurred, to signal the controller 110 to complete the circuit and supply high-frequency electrical current to the induction coil 108. Alternatively, the slider or user interface 136 can have an electrical contact that completes the electrical circuit from the energy source 106 to the induction coil 108, enabling the controller 110 to control the supply of energy to the induction coil 108.

Supplying energy to the induction coil 108 generates an intense, oscillating magnetic field in the middle of the induction coil 108. Because of the presence of the metal medical sharp (i.e., the stainless steel pen needle cannula 144) within the coil 108, the oscillating magnetic field induces electrical eddy currents in the metal medical sharp which in turn cause resistance heating of the sharp. The heating softens and weakens the adhesive and/or the plastic connecting the medical sharp 144 with the holder 142 (in this example, plastic pen needle hub 142). A preferred configuration of the induction coil 108, in particular a configuration that comprises a larger diameter upper coil portion 160 axially spaced from a smaller-diameter lower coil portion 162, is best seen in FIG. 4. This stepped coil shape mirrors the stepped distal configuration of a typical pen needle, and allows the RF energy produced by the coil to be applied as closely as possible to the adhesive and/or plastic material at the interface between the metal needle cannula 144 and the plastic hub 142.

Because the collet 122 is being pushed down by the force applied by the user to the slider 136, once the connection between the needle 144 and the hub 142 is sufficiently softened and weakened by the induced heating to permit displacement of the needle 144 relative to the hub 142, the collet 122, which is still gripping the needle 144, pulls the needle 144 downward and free of the hub 142. As the collet 122 travels downwardly in a tapered section of the interior of a columnar portion 118 of the receiving unit 114, the radially inward force applied to the sharp receiving portion of the collet, and thus, the collet's grip on the needle 144, decreases. In other words, the tapered shape of the tapered section permits the collet 122 to expand as it travels in the first direction (i.e., downward in the figures). The location of the tapered section is chosen so that the collet 122 is allowed to expand to release the needle 144 only after the needle has been fully pulled free from the plastic hub 142.

According to one embodiment, the state in which the connection between the needle 144 and the hub 142 is sufficiently softened and weakened by the induced heating to permit displacement of the needle 144 relative to the hub 142 is achieved rather suddenly, and the collet 122 imparts momentum to the needle. Once the grip of the collet 122 decreases sufficiently, the collet 122 releases the needle 144, and the momentum of the needle 144 carries it into the sharps receiving container 124.

Subsequently, the user releases the downward force applied to the slider 136, and the first spring 130 returns the collet 122 and the slider 136 to the initial position shown in FIGS. 2 and 4. Alternatively, the user can return the slider 136 (and thus the collet 122 due to their coupling) to the initial position shown in FIGS. 2 and 4.

According to one embodiment, the controller 110 supplies energy to the induction coil 108 for a predetermined amount of time. Alternatively, the controller can control the energy supply to the induction coil 108 based on the position of the slider 136 or the collet 122 (for example, via sensors or electrical contacts previously described, or via different sensors).

Once the needle 144 is separated from the hub 142, the user can open the door member 134 and remove the hub 142 from the device 100 for disposal or recycling, while the needle 144 is safely disposed in the sharps receiving container or chamber 124. The heating applied to the needle 144 before its separation from the hub 142, although brief, may have the effect of sterilizing the needle 144 and thereby rendering it less hazardous during any subsequent handling and disposal. The opening of the sharps receiving container 124 may be provided with a rubber septum-like barrier or duckbill valve that is opened by a wedge or cone when the container 124 is attached to the body 102 of the device 100, allowing the needle 144 to enter the container 124. When the container 124 is removed for disposal, the septum or valve will spring closed so that the needle 144 and any other separated sharps in the container 124 are retained therein and cannot fall out.

In the illustrated example of FIGS. 1-4, the medical sharp is the metal pen needle cannula 144 and the holder is the plastic pen needle hub 142. But other medical sharps and holders can also be separated using the device 100. In general, any medical device having a potentially hazardous metal sharps component that needs to be separated from a plastic holder and contained for disposal can be accommodated by the device 100. For example, a metal lancet, stylet or trocar can be separated from its handle, a metal needle cannula can be separated from a staked syringe or from a hub or holder that is fitted to a syringe, and a metal catheter introducer needle can be separated from its hub or holder. A cutout 146 (best seen in FIG. 1) in the door member 134 accommodates a lancet, stylet or trocar handle, a syringe, or a catheter introducer while the device 100 is used to separate the medical sharp from its holder, and still permit the door member 134 to close. Similarly, the shape of the receiving unit 114 may be altered to accommodate these different types of medical devices by providing a snug fit between the receiving unit 114 and the plastic holder or handle to which the metal sharp is attached.

The body 102, the receiving unit 114, the collet 122, the door member 134, the slider 136, and the sharps receiving container 124 can be made of plastic, such as polypropylene (PP), polyethylene (PE), polycarbonate (PC), acrylonitrile butadiene styrene (ABS), or polyether ether ketone (PEEK). Different components can be made of different plastics. Preferably, the collet 122 is ceramic, or is made of metal, such as aluminum.

Embodiments of the present invention, with the induction coil, are particularly useful in situations wherein direct access to multiple contact points on a medical sharp are difficult, thereby making a conductive heating mechanism less achievable.

Embodiments of the present invention provide a portable personal sharps container and removal device that allows for safe containment and disposal of contaminated sharps, and can improve needle disposal compliance of needle users.

Embodiments of the present invention can operate by removing only the metal sharps portion of the injection device (for example, pen needle or syringe but not limited thereto) and retaining the metal shams portion inside the device while allowing the user to discard the plastic non-sharps components as regular trash or recyclable content. Embodiments of the present invention can achieve this effect by inductively generating an area of intense high temperature near, for example, the adhesive bead that adheres the medical sharp to the holder, in conjunction with a "pull-out" mechanism.

In embodiments of the present invention, the heating can be achieved by an induction heating mechanism. With such a mechanism, the needle does not need to be directly contacted by the heating mechanism. However, the heating can also be achieved in other ways, such as by a heating element directly contacting the medical sharp, or by contacting the medical sharp to complete an electrical circuit to pass a current through the medical sharp, See, for example, commonly-assigned U.S. Pat. Nos. 8,829,394, 9,579,469 and 9,802,006, the entire disclosures of which are expressly incorporated herein by reference.

In some embodiments of the present invention, the device 100 has a durable component and a disposable component. The durable component utilizes a power source, such as a battery (rechargeable or otherwise). An indicator can be incorporated into the device that alerts the user when the cannula holding compartment has reached a certain capacity. A similar feature can used to manage power requirements, such as battery replacement or recharging. The disposable component (chamber or sharps receiving portion) can be utilized until an adequate number of needles has been introduced into the chamber, after which it can be detached and disposed of appropriately. Appropriate disposal can include a variety of options, for example, the disposable component can be mailed to the manufacturer or a separate waste management entity, or the disposable component can be thrown away in an appropriate medical disposal receptacle. Preferably, replacement disposable components can be obtained to continue using the durable component for subsequent medical sharps removal.

Figure 5:
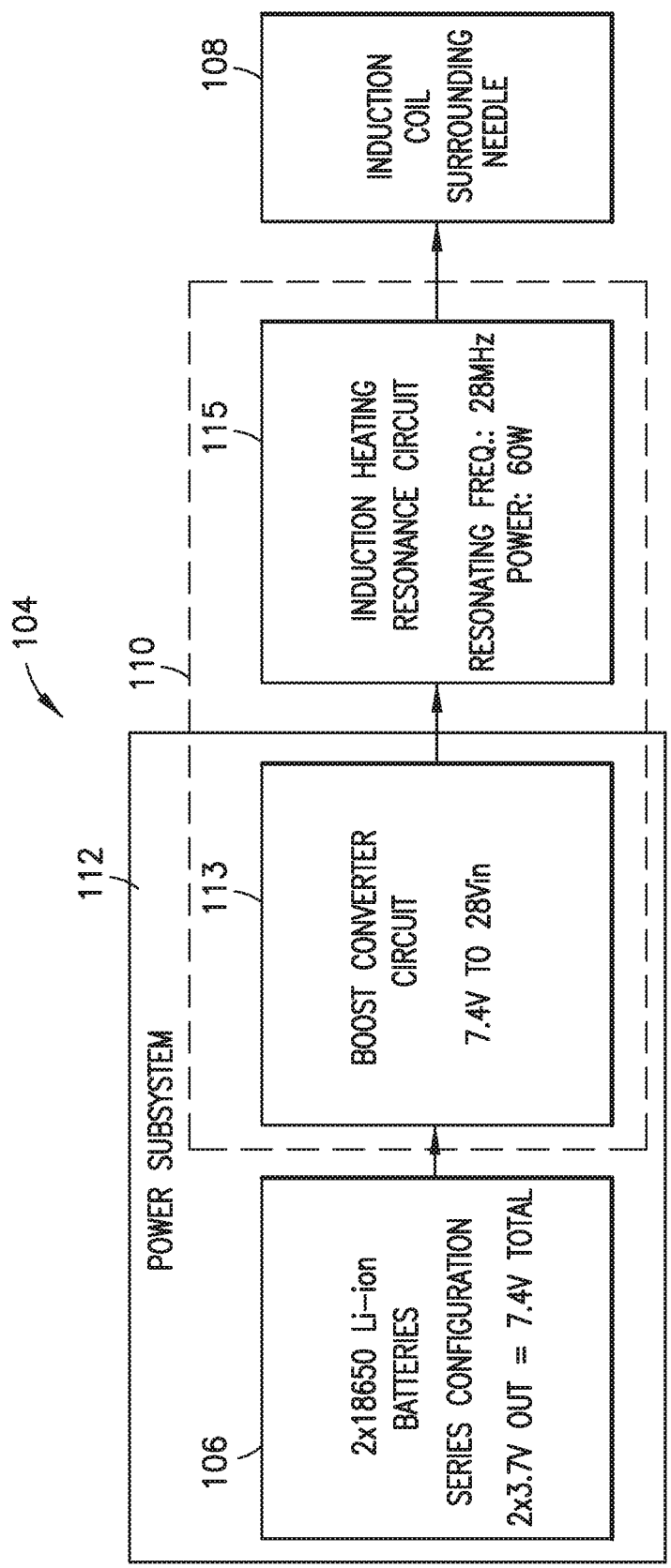
FIGS. 5 and 6 are block and schematic diagrams of a first embodiment of an electrical control circuit for the exemplary device of FIGS. 1 and 2.

FIG. 5 is a block diagram of a first exemplary electrical control circuit for the device 100 of FIGS. 1 and 2. The heating unit 104 can be configured as a power subsystem 112 that includes the energy source 106 and a DC chopper-type boost converter circuit 113. According to one embodiment, the boost converter circuit 113 and an induction heating resonance circuit 115 are part of the controller 110. In one embodiment, the energy source 106 includes a one or more batteries, such as two 3.7-volt lithium-ion batteries connected in series. The boost converter circuit 113 converts the 7.4-volt DC output of the two series-connected lithium-ion batteries to a 28-volt DC output. One skilled in the art will appreciate that other battery configurations or other types of batteries can be employed without departing from the scope of the present invention. According to one embodiment, the energy source 106 is removable from the body 102, and is replaceable. Although not shown in FIG. 5, the power subsystem 112 may be controlled by one or both of the previously mentioned sensors 182, 184, or in some other manner, so that it applies power to the induction heating resonance circuit 115 only when the user has properly inserted a medical sharp and has activated the collet 122.

Figure 6A:
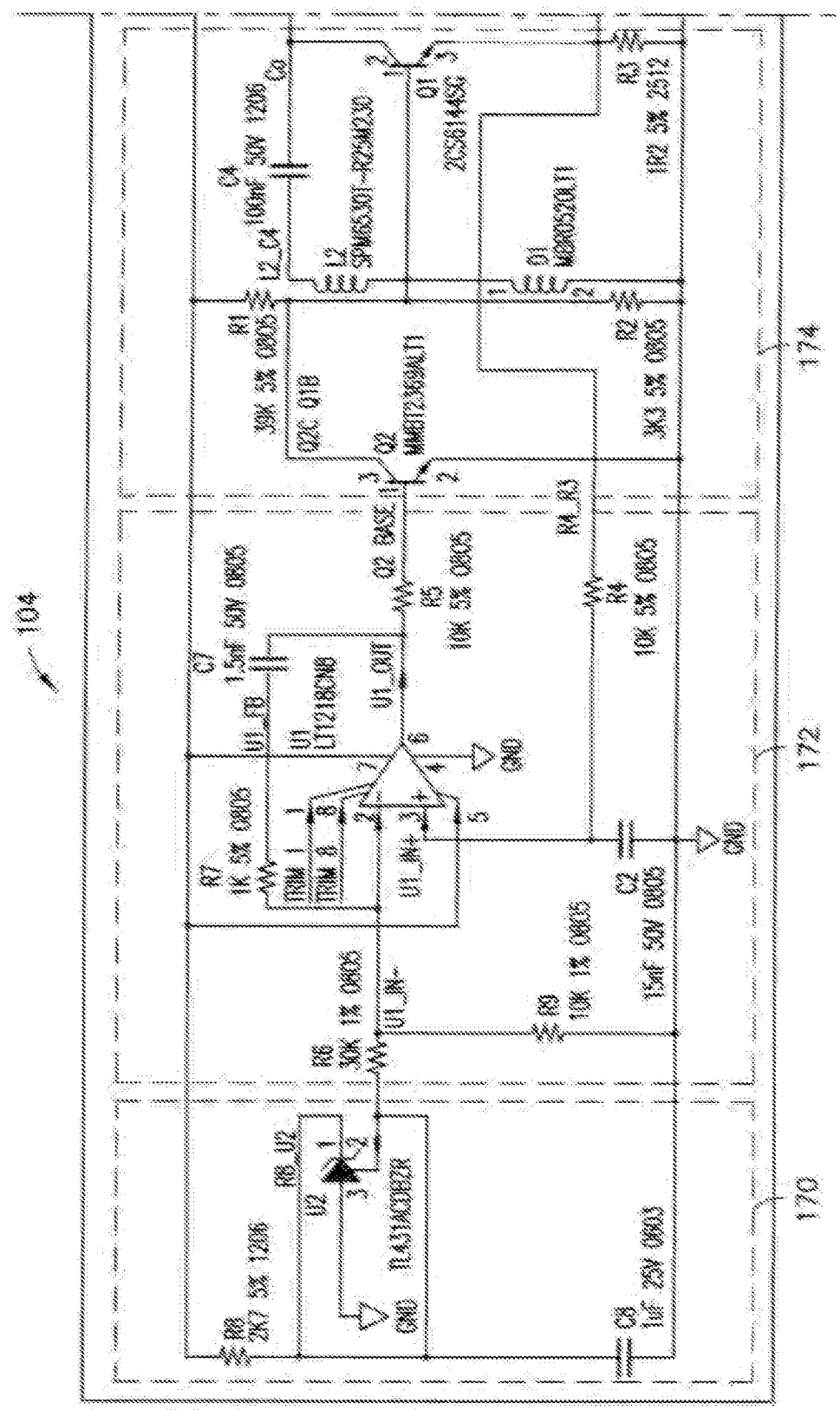
Figure 6B:
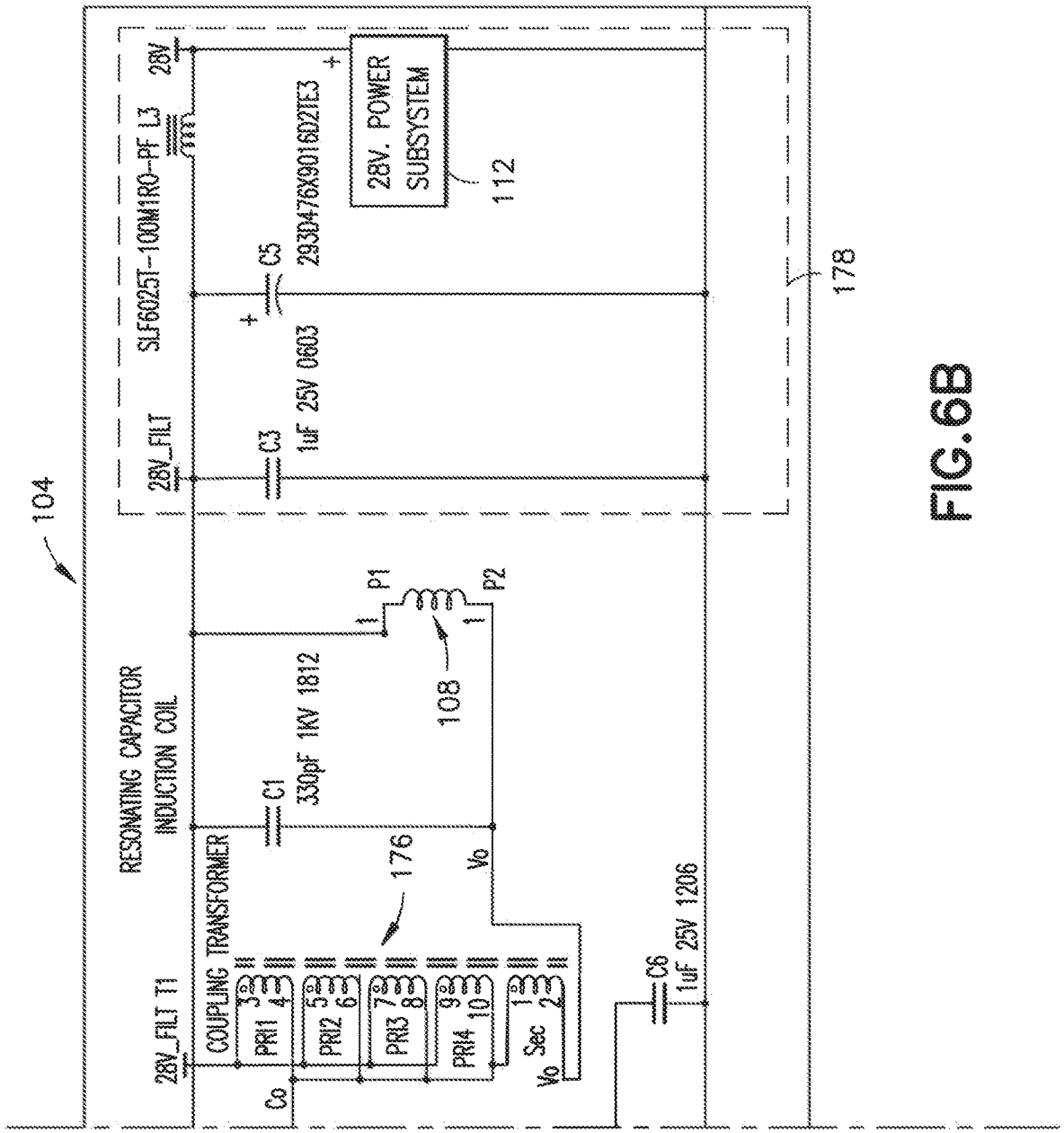

FIG. 6 is a detailed schematic diagram of the electrical control circuit of FIG. 5. The voltage reference circuit 170 utilizes a Zener diode U2 to produce a low voltage reference that controls the frequency of the induction oscillator (tank circuit), This voltage reference is provided as an input to an oscillator drive circuit 172 that utilizes an operational amplifier (op amp) U1 in combination with the illustrated trimming resistors and capacitors to produce the desired oscillation frequency of 27 MHz. The output of the op amp U2 is applied as an input to a drive (amplifier) circuit 174 that uses bipolar transistors Q1 and Q2 to provide the desired output power (about 60 watts) to a coupling transformer 176. The coupling transformer 176 provides a voltage boost and impedance match to the magnetic induction heating coil 108 of the needle removal device 100. The power supply 178 filters and smoothes the 28-volt DC output from the batteries 106 and boost converter circuit 113 that constitute the 28-volt power subsystem 112.

It should be noted that frequencies other than 27 MHz can be used, with corresponding changes to the drive circuit and induction coil geometry. For example, 43 MHz is another unlicensed frequency that is suitable for use in the present invention. In general, frequencies in the unlicensed ISM bands are preferred, although this is not essential.

Figure 7:
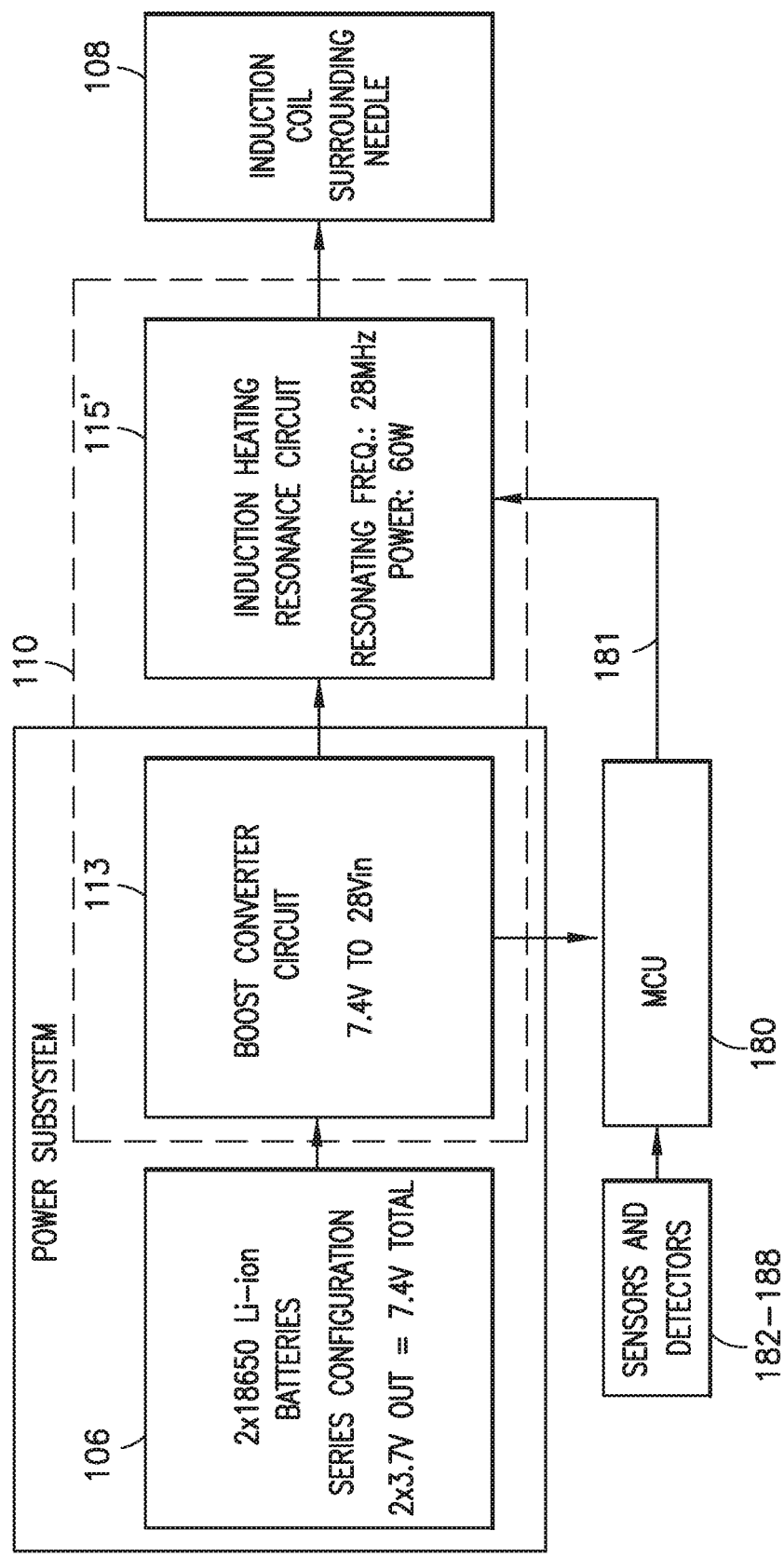
FIGS. 7 and 8 are block and schematic diagrams of a second embodiment of an electrical control circuit for the exemplary device of FIGS. 1 and 2.
Figure 8A:
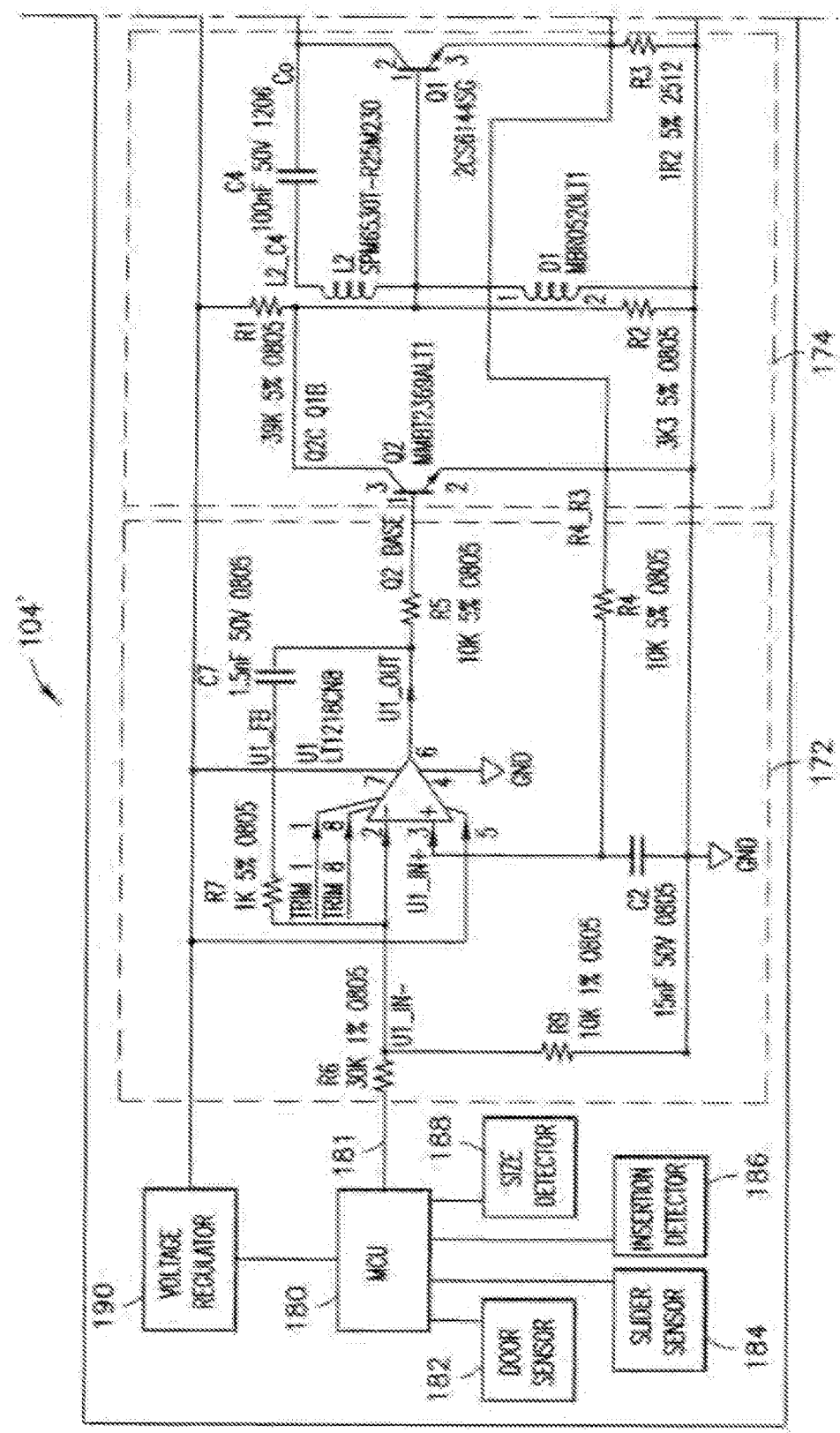
Figure 8B:
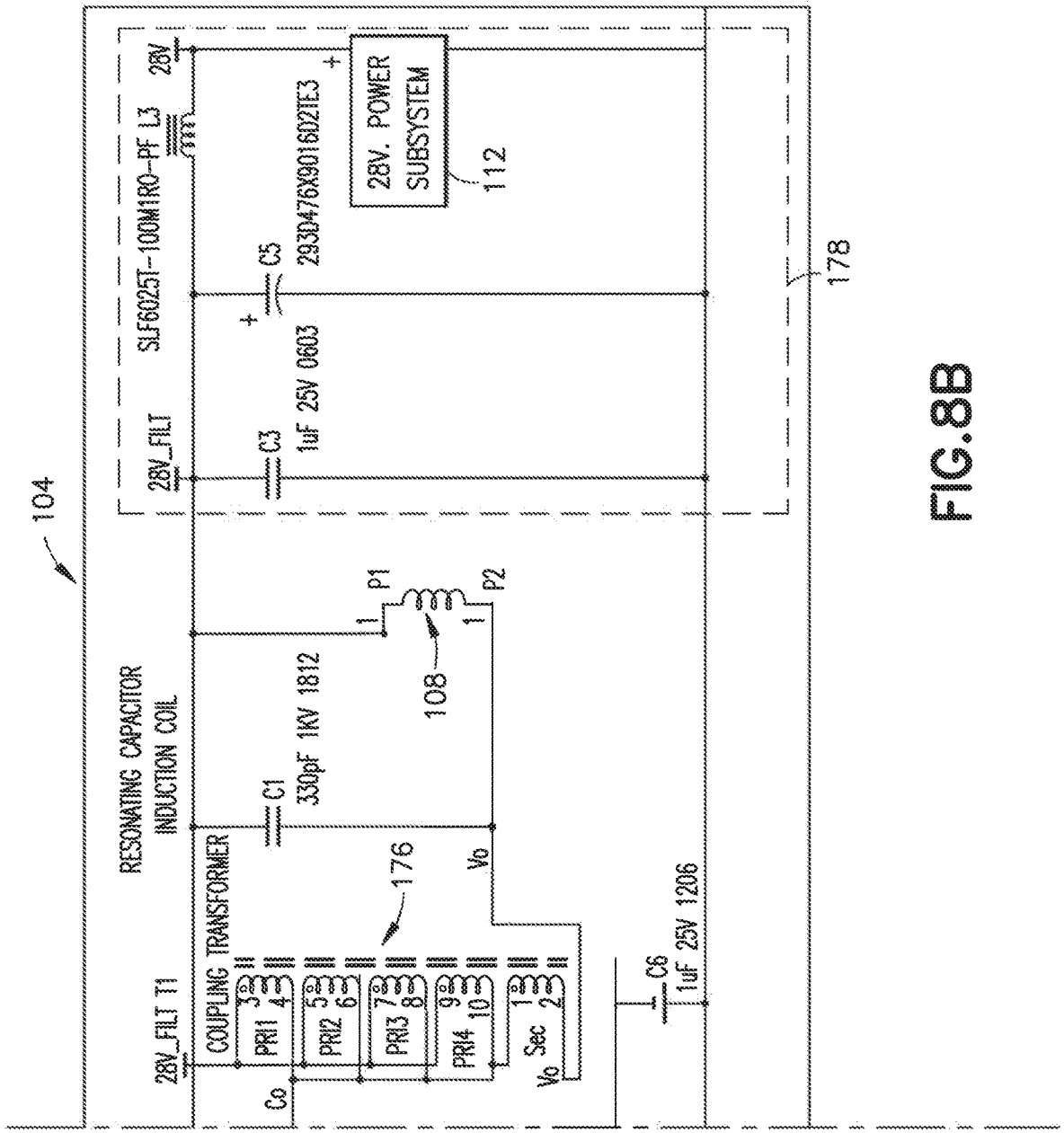

FIG. 7 is a block diagram of a second exemplary electrical control circuit for the device of FIGS. 1 and 2. In this circuit, a microcontroller unit (MCU) 180 is used to control the functions of the circuit, including varying the oscillation frequency of the resonant circuit and sensing the state of various sensors and detectors 182-188. FIG. 8 is a detailed schematic diagram of this embodiment, in which the voltage reference circuit 170 is deleted and replaced by a digital-to-analog converted (DAC) output from the MCU 180. The voltage level on the line 181 controls the oscillation frequency of the magnetic induction coil 108 and hence the amount of RF power applied to the sharp that is being separated from its holder. The MCU receives inputs from the sensor 182 for detecting the position of the door member 134, the sensor 184 for detecting the position of the slider 136, a needle insertion detector 186, and a needle size detector 188. The sensors 186 and 188 can be combined into a single sensor in some embodiments. A voltage regulator 190 coupled to the power subsystem 112 provides the required DC supply voltage to the MCU 180.

Figure 9:
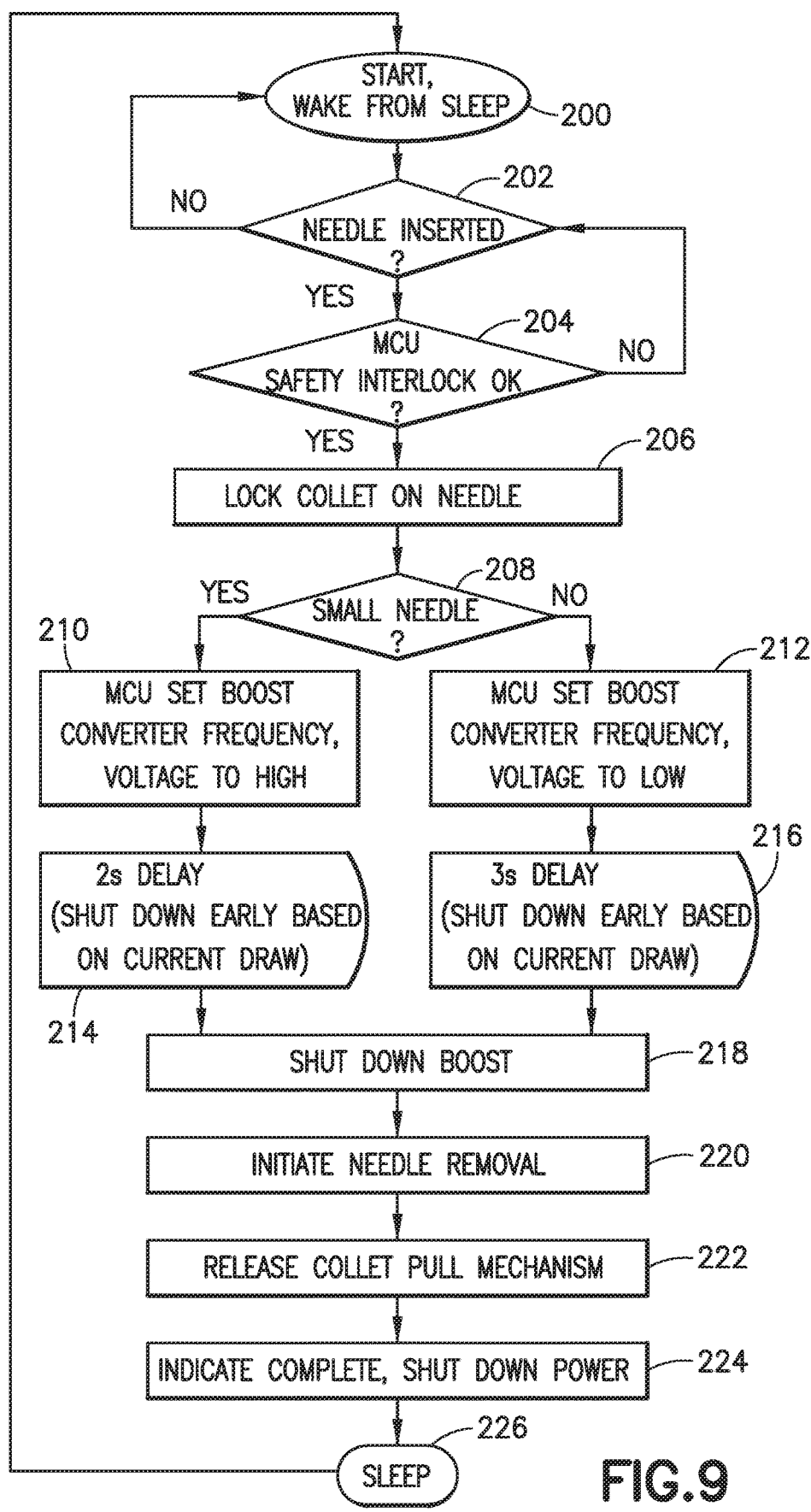
FIG. 9 is a flow chart illustrating the operation of the electrical control circuit of FIGS. 7 and 8.
Figure 10A:
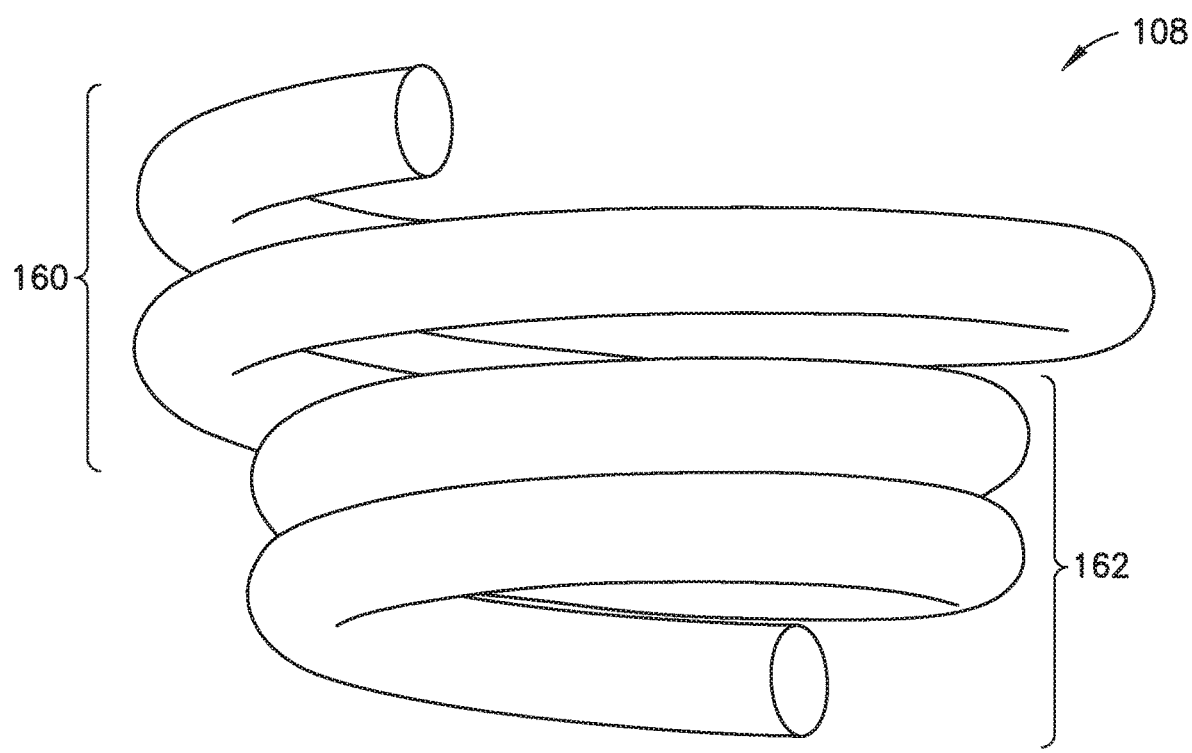
FIGS. 10A and 10B illustrate two possible shapes for the magnetic induction coil used in the exemplary device of FIGS. 1 and 2.
Figure 10B:
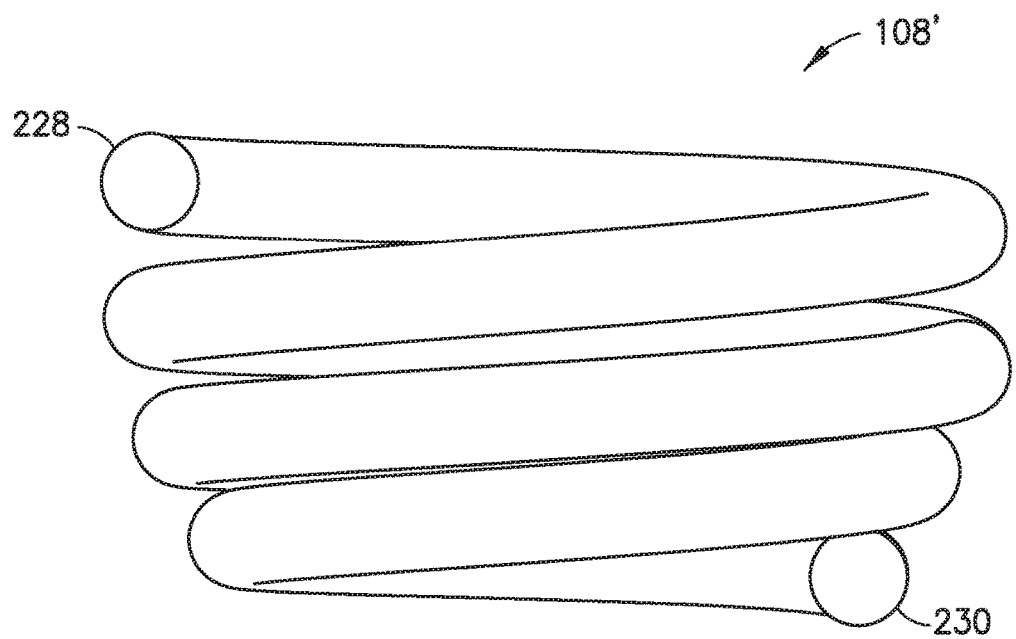

FIG. 9 is a flowchart which describes the operation of the device 100 of FIGS. 1 and 2 when provided with the MCU-based control circuit of FIGS. 7 and 8. Upon waking from a sleep state at 200, the MCU checks at 202 to determine whether a needle has been inserted by detecting the state of the needle insertion detector 186, which can take the form of an electrical (e.g., inductive or capacitive), mechanical or optical sensor. If it has, the MCU then verifies at 204 that the safety interlock 182 for the door member 134 has been activated. After the collet 122 has locked onto the pen needle cannula 144 at 206, the MCU checks the size (gauge) of the cannula at 208 to determine whether it is large or small. This is done using the needle size detector 188, which can also take the form of an electrical (e.g., inductive or capacitive mechanical or optical sensor. As previously noted, the sensors 186 and 188 can be combined into a single sensor. If the needle is determined to be of small gauge, the MCU applies at 210 a higher boost converter frequency and voltage for a shorter period of time (e.g., 2 seconds), whereas if the needle is determined to be of large gauge, the MCU applies at 212 a lower boost converter frequency and voltage for a longer period of time (e.g., 3 seconds). Since the needle is acting as a resonance antenna, these parameters produce optimal resonance and inductive coupling for the respective needle sizes. In both cases, the MCU has the ability to shut down the oscillation early at 214, 216 if the current draw is determined to be excessive (this determination can be via a temperature sensor or by direct measurement of the current draw). After the predetermined duty cycle (on time), the output to the induction coil 108 is terminated by the MCU at 218, the cannula 144 is removed at 220, the collet 122 mechanism is released at 222, an audible or visible completion signal is generated and power to the control circuit is shut down at 224, and the processor re-enters a sleep state at 226, FIG. 10A is a detailed view of the induction coil 108 illustrating the larger diameter upper coil portion 160 and the axially-spaced, smaller-diameter lower coil portion 162 which together provide the coil with a stepped shape in side view. Although this coil shape is preferred, other coil geometries are possible. For example, a conical geometry in which the induction coil 108' tapers more gradually in the axial direction from the top 228 to the bottom 230 is illustrated in FIG. 10B.

Although only a few embodiments of the present invention have been shown and described, the present invention is not limited to the described embodiments. Instead, it will be appreciated by those skilled in the art that changes may be made to these embodiments without departing from the principles and spirit of the invention. Any of the embodiments and/or elements disclosed herein may be combined with one another to form various additional embodiments not specifically disclosed, as long as they do not contradict each other. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

The invention claimed is:

1. An apparatus for removing a medical sharp from a holder, comprising:
    a magnetic induction coil; and
    a control circuit for energizing said magnetic induction coil;
    wherein said magnetic induction coil has a stepped shape defined by two axially spaced portions having different diameters, or a conical shape defined by a gradually changing diameter in the axial direction, said magnetic induction coil having a shape corresponding to a shape of the holder and for surrounding the holder and portion of the medical sharp received in the holder.

2. The apparatus according to claim 1, wherein the medical sharp comprises a metal pen needle cannula and the holder comprises a plastic pen needle hub.

3. The apparatus according to claim 1, wherein the control circuit energizes the magnetic induction coil at a frequency of about 27 MHz or about 43 MHz.

4. The apparatus according to claim 1, wherein the control circuit includes a micro controller unit.

5. An apparatus for removing a medical sharp from a holder, comprising:
    a magnetic induction coil configured for surrounding the holder and a portion of the medical sharp received in the holder; and
    a control circuit for energizing said magnetic induction coil;
    wherein the control circuit energizes the magnetic induction coil at a frequency of about 27 MHz or about 43 MHz.

6. The apparatus according to claim 5, wherein the medical sharp comprises a metal pen needle cannula and the holder comprises a plastic pen needle hub.

7. The apparatus according to claim 5, wherein the magnetic induction control circuit includes a micro controller unit.

8. An apparatus for removing a medical sharp from a holder, comprising:
    a magnetic induction coil configured for surrounding the medical sharp and the holder; and
    a control circuit for energizing said coil;
    wherein the control circuit energizes the magnetic induction coil at a voltage and/or frequency that is at least partly dependent on the size or gauge of said medical sharp.

9. The apparatus according to claim 8, wherein the medical sharp comprises a metal pen needle cannula and the holder comprises a plastic pen needle hub.

10. The apparatus according to claim 8, wherein the control circuit includes a micro controller unit.

11. An apparatus for removing a medical sharp from a holder, comprising:
    a magnetic induction coil configured to receive and surround the holder and the medical sharp;
    a control circuit for energizing the magnetic induction coil;
    a housing for enclosing the magnetic induction coil and the control circuit and configured for receiving the medical sharp and holder;
    a movable door for providing access to the housing; and
    a sensor coupled to the control circuit for detecting an open or closed state of the movable door; and
    a movable collet for gripping the medical sharp when the collet is in a first position and being movable to a second position to separate the medical sharp from the holder.

12. The apparatus according to claim 11, wherein the medical sharp comprises a metal pen needle cannula and the holder comprises a plastic pen needle hub.

13. The apparatus according to claim 11, wherein the control circuit energizes the coil at a frequency of about 27 MHz or about 43 MHz.

14. The apparatus according to claim 11, wherein the control circuit includes a micro controller unit.

15. An apparatus for removing a medical sharp from a holder, comprising:
    a magnetic induction coil;
    a control circuit for energizing the magnetic induction coil at an RF frequency;

a housing for enclosing the magnetic induction coil and the control circuit where the magnetic induction coil surrounds a tip of the holder and the medical sharp received in the holder;
a movable door for providing access to the housing; and
a metallic shield on the movable door for reducing RF emissions from said housing.

16. The apparatus according to claim 15, wherein the medical sharp comprises a metal pen needle cannula and the holder comprises a plastic pen needle hub.

17. The apparatus according to claim 15, wherein the RF frequency is about 27 MHz or about 43 MHz.

18. The apparatus according to claim 15, wherein the control circuit includes a micro controller unit.

19. The apparatus of claim 15, further comprising a collet configured to grip the medical sharp when the medical sharp and holder are inserted into the apparatus and the collet is in a first position, and where the collet is movable to a second position to separate the medical sharp from the holder when the medical sharp is heated to a temperature to release the medical sharp from the holder.

20. The apparatus of claim 19, further comprising a column for receiving the collet in the first position where the collet grips the medical sharp in the first position, and the where the collet is movable to the second position where the medical sharp separates from the collet.

21. The apparatus of claim 20, further comprising a manual user interface for moving the collet from the first position to the second position.

22. The apparatus of claim 21, further comprising a first spring extending between said collet and said user interface where said first spring is in a loaded state when said user interface is moved from the first position to the second position.

23. The apparatus of claim 22, further comprising a second spring to bias said collet toward said column to said first position.

24. The apparatus of claim 23, wherein said user interface in said second position compresses said first spring to apply a force on said collet where heating the medical sharp to a temperature sufficient separates the medical sharp from the holder, and where said first spring has a biasing force in the loaded state to move the collet to the second position against second spring to separate the medical sharp from the holder.

* * * * *